(12) United States Patent
LaHaye

(10) Patent No.: US 6,322,555 B1
(45) Date of Patent: *Nov. 27, 2001

(54) METHOD AND APPARATUS FOR MONITORING LASER SURGERY

(76) Inventor: Leon C. LaHaye, 3155 I-49 S., Opelousas, LA (US) 70570

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/359,371
(22) Filed: Jul. 23, 1999
(51) Int. Cl.[7] ................................. A61B 18/18
(52) U.S. Cl. ................... 606/5; 606/10; 606/11; 606/12; 128/898; 219/121.6; 250/252.1; 356/302; 356/307
(58) Field of Search ............ 606/10–12, 2, 606/3–6; 219/121.61–121.63, 121.6; 128/898; 250/252.1; 356/302, 307

(56) References Cited

U.S. PATENT DOCUMENTS

| | | | |
|---|---|---|---|
| 4,061,925 | * 12/1977 | Van Der Gaag et al. | 250/553 |
| 4,695,697 | * 9/1987 | Kosa | 219/121 |
| 4,729,372 | 3/1988 | L'Esperance, Jr. . | |
| 4,784,135 | 11/1988 | Blum et al. . | |
| 4,792,690 | * 12/1988 | McCann et al. | 250/474.1 |
| 4,941,093 | 7/1990 | Marshall et al. . | |
| 4,973,330 | 11/1990 | Azema et al. . | |
| 4,994,059 | * 2/1991 | Kosa et al. | 606/12 |
| 5,002,051 | * 3/1991 | Dew et al. | 128/395 |
| 5,012,202 | * 4/1991 | Taylor | 330/284 |
| 5,108,388 | 4/1992 | Trokel . | |
| 5,123,902 | * 6/1992 | Muller et al. | 604/21 |
| 5,154,707 | * 10/1992 | Rink et al. | 606/12 |
| 5,196,006 | 3/1993 | Klopotek et al. . | |
| 5,219,343 | 6/1993 | L'Esperance, Jr. . | |
| 5,219,344 | 6/1993 | Yoder, Jr. . | |
| 5,225,884 | * 7/1993 | Stark et al. | 356/73 |
| 5,324,281 | 6/1994 | Muller . | |
| 5,423,801 | 6/1995 | Marshall et al. . | |
| 5,464,960 | 11/1995 | Hall et al. . | |
| 5,752,950 | * 5/1998 | Frey et al. | 606/12 |
| 5,772,656 | 6/1998 | Klopotek . | |
| 5,891,131 | 4/1999 | Rajan et al. . | |
| 5,984,916 | * 11/1999 | Lai | 606/11 |
| 6,074,382 | * 6/2000 | Asah et al. | 606/9 |
| 6,080,148 | * 6/2000 | Damasco et al. | 606/10 |
| 6,090,100 | * 7/2000 | Hohla | 606/5 |
| 6,099,522 | * 8/2000 | Knopp et al. | 606/10 |

OTHER PUBLICATIONS

SVS Apex, 6.5mm Holmium;/Excimer Laser System User's Manual, Operation and Maintenance, Rev. B, pp. 2–15, 26, 27, 3–11, 6–11 through 6–13, 6–14 through 6–17, 6–25 through 6–38, 8–4 through 8–8, 8–19, through 8–25, 9–1, 2, 8, 10, 11, and 13, (Summit Technology, Inc.) (Jan. 1995).

PM1 Calibration Procedure Service Manual, pp. 5.3–1 through 5.3–5, 5.4–1 through 5.4–6, and Star Printout Customer Information (Summit Technology, Inc.) (Jan. 1995).

Dr. Leon C. LaHaye, Continuation-in-Part application of 09/359,371 filed on Jul. 23, 1999, pp. 1–31 and 8 sheets of drawings, (Mar. 26, 2001).

* cited by examiner

Primary Examiner—Lee Cohen
Assistant Examiner—A. Farah
(74) Attorney, Agent, or Firm—Burns, Doane, Swecker & Mathis, L.L.P.

(57) ABSTRACT

A method and system for laser surgery produces controlled laser pulses and simultaneously verifies that a sequence of pulses of prescribed energy are being delivered to the patient. A photo detector receives a predetermined portion of the energy of each treatment pulse. A separate monitoring computer compares an output signal from the photo detector corresponding to each treatment laser pulse with a reference value for that type of pulse obtained in a calibration sequence. Implementation in an ophthalmic laser surgery system is also disclosed.

25 Claims, 4 Drawing Sheets

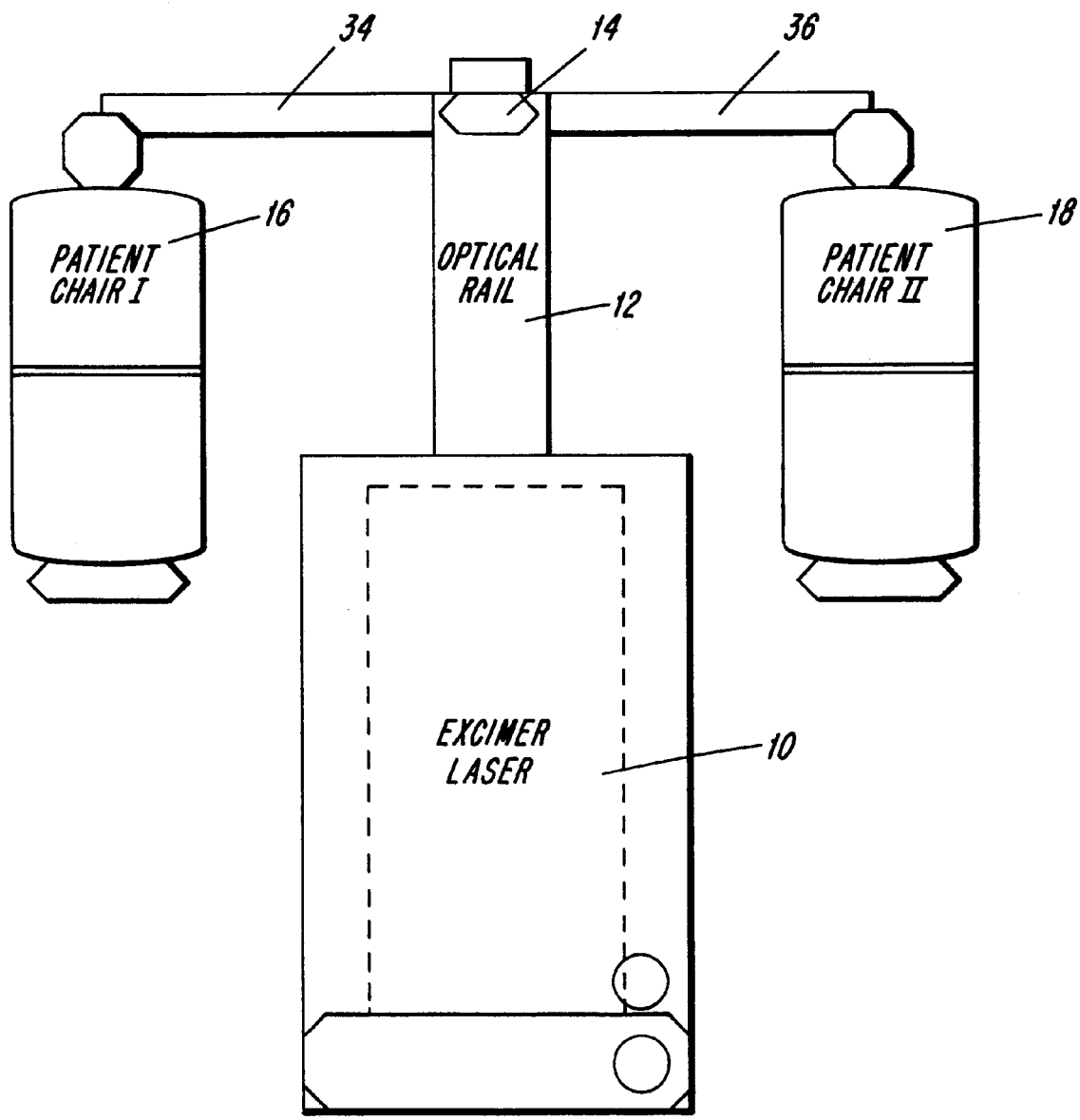

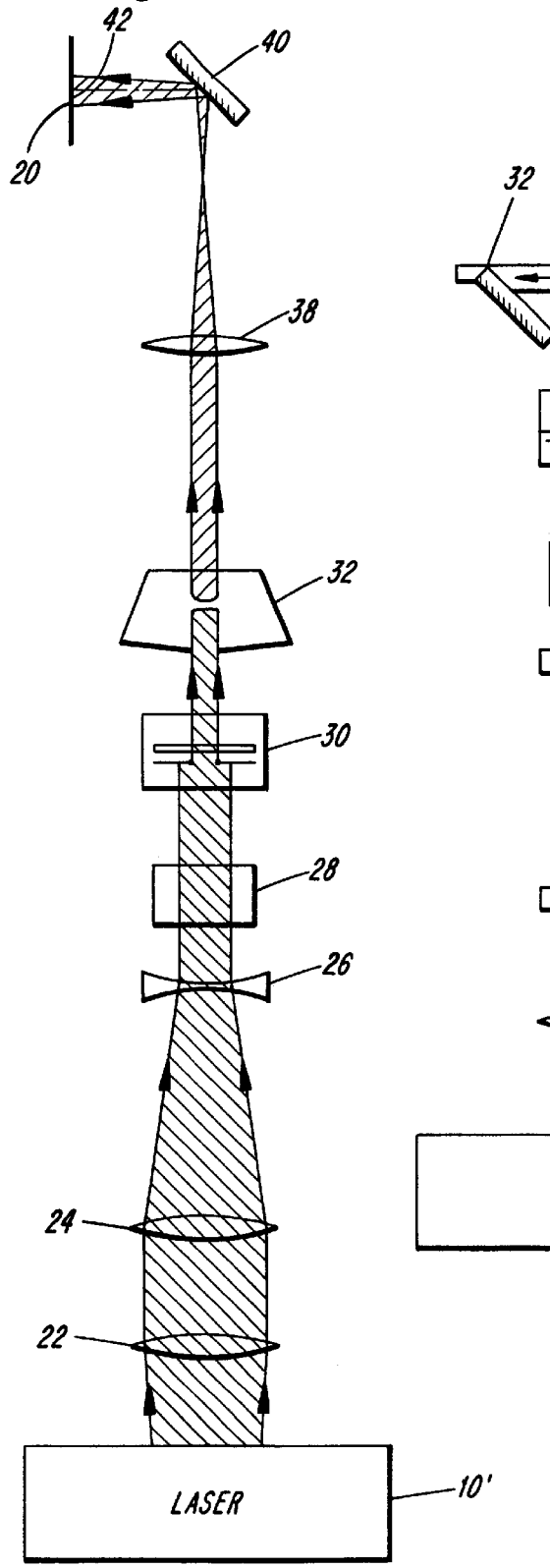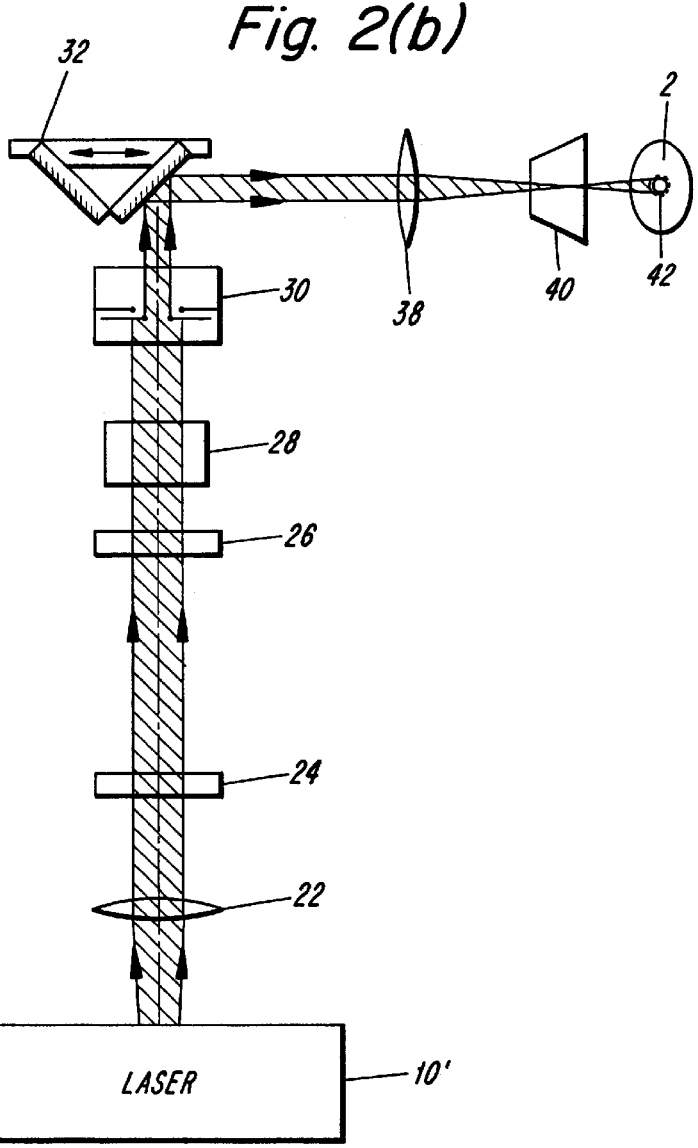

METHOD AND APPARATUS FOR MONITORING LASER SURGERY

FIELD OF THE INVENTION

This invention relates to laser surgery apparatus and methods and more particularly to the monitoring of laser systems used in ophthalmic laser surgery.

BACKGROUND OF THE INVENTION

Laser systems have been used in ophthalmic surgery for modifying the cornea of the patient. Systems such as shown in U.S. Pat. No. 4,729,372 to L'Esperance contemplate the controlled ablation of the cornea of the patient with a pulsed excimer laser. Operations performed with the system include corneal transplants and keratotomies.

The application of laser light to the cornea may be controlled by spot scanning of the cornea or by the use of masks. As shown in U.S. Pat. No. 5,108,388 to Trokel, the masks may, for example, employ slits or holes. Repeated scanning or pulsing through properly selected masks are employed to reshape or reprofile the curvature of the cornea to treat myopic or hyperopic conditions. The system can also be used, for example, to remove corneal sections for corneal replacements or transplants.

A system used by applicant for performing ophthalmic laser surgery is shown in FIG. 1. The system includes an Excimer laser 10 such as a COMPex 201 Excimer laser. An optical rail 12 contains optical elements for controlling the laser pulses and delivers spatially modulated pulses to a shuttling device 14, which acts as a selectively positionable turning mirror, for directing the laser pulses to a selected one of the two surgical stations, 16 and 18. The system allows surgery to be performed on one patient while a second patient is readied, and improves the utilization efficiency of the operating room, laser and optical rail.

FIGS. 2(a) and (b) are vertical and horizontal cross-sectional views and ray traces of an optical path which may be used in the system of FIG. 1 to deliver pulses from the laser 10' to the cornea of the patient at 20. A light beam from the laser is shaped and focused by a series of lenses 22, 24 and 26. A beam homogenizer 28 is located next in the optical path as shown. A spatial modulator 30 provides beam dimensions and orientations in accordance with predetermined treatment parameters appropriate for the surgery required by the patient. The spatial modulator may include a conventional iris and variable, slit mask(s) as well as controls for changing the axis of orientation of the mask(s). These systems are motor driven on command from a treatment computer containing a treatment algorithm into which the treatment parameters have been programmed.

The shuttling turning mirror 32 selectively directs the laser beam to one or the other surgical stations along one of the system arms 34 or 36 shown in FIG. 1. An imaging lens 38 is located in each arm. Pulses from the imaging lens are reflected by end turning mirror 40 toward the target area 42 on the patient's cornea.

It is important that pulses delivered to the cornea have the appropriate energy to ensure that the reprofiling, cutting or ablation produced is consistent with the prescribed treatment for the patient. Systems of the type shown in FIG. 2 have employed photo detectors selectively positionable in the main optical path of the system at the end turning mirror for the purpose of calibrating or adjusting the energy delivered by the system during a preliminary calibration phase. See U.S. Pat. No. 5,772,656 to Kloptek.

Other control systems have been proposed such as disclosed in U.S. Pat. No. 4,941,093 to Marshall et al., which includes a measurement device to measure the cornea surface profile and a feedback control system to control the laser operation in accordance with the measured and desired profiles. U.S. Pat. No. 5,423,801 to Marshall et al. discloses further control of the laser by a measurement signal from a beam-shaping means and/or cornea while it is exposed to irradiation by the laser. U.S. Pat. No. 4,973,330 to Azema et al. discloses a photo detector associated with a semi-transparent mirror, which is intended to furnish a treatment computer with information relative to the energy of the pulses exiting the laser before the laser beam reaches the controlling device. A laser calibration device is shown in U.S. Pat. No. 5,464,960 to Hall et al. which employs a phantom cornea with superimposed thin films of alternating colors.

OBJECTS AND SUMMARY OF THE INVENTION

It is an object of the present invention to provide a more efficient and reliable technique for monitoring laser surgery.

It is another object of the present invention to monitor the energy of actual laser pulses used in the ophthalmic laser surgery after spatial modulation.

It is another object of the present invention to monitor a sequence of laser pulses of varying beam dimensions used in ophthalmic laser surgery.

It is another object of the present invention to provide a parallel, fail-safe system for detecting discrepancies between a programmed treatment and the laser pulses actually administered to the cornea of the patient.

These and other objects and features will be apparent from the following description of the present invention contained herein.

The present invention relates to methods for laser surgery and particularly for the modification of the cornea of a patient with a laser system in accordance with treatment parameters appropriate for the patient and for continuously verifying that a predetermined sequence of laser pulses of correct energy are being delivered to the cornea of the patient. In practicing the method, pulses of laser light are generated and controlled. The controlled pulses are simultaneously directed to the cornea of the patient and to a photo detector. An output signal of the photo detector is converted into a value representative of the light energy delivered to the cornea of the patient.

The light energy value may be compared to a reference value derived from system calibration information and from the treatment parameters for the patient. An indication of the performance of the laser system is provided in response to this comparison.

In preferred embodiments of the method, the pulses of laser light are produced by a laser triggered by a triggering signal from a treatment computer. The pulses of laser light may be spatially modulated responsive to signals from the treatment computer. The treatment computer is programmed with the treatment parameters appropriate for the patient.

In this embodiment, the reference value is produced by a monitoring computer separately programmed with the treatment parameters appropriate for the patient. The double entry of treatment parameters helps expose data entry errors in the treatment computer, since such an error will create a discrepancy between the light energy value and the reference value. The comparison may be initiated by the monitoring computer responsive to the laser triggering signal. When the light energy value of a predetermined number of pulses deviates a predetermined amount from the corresponding reference values, the system may produce an alarm signal or shut down the system.

In another preferred embodiment of the present invention, the simultaneous directing of the spatially modulated pulses is performed by beam-splitting the pulses to direct a portion of electromagnetic energy from the pulse to a photo detector. The directed portion of electromagnetic energy of the laser pulse is converted to fluorescent light which is detected by the photo detector. One or more neutral density filters may be employed to filter the fluorescent light so that the photo detector and associated amplifier are operated in a generally linear response mode across a range of expected incident radiation energies.

The present invention also includes an apparatus for producing a predetermined treatment sequence of laser pulses of predetermined energy and for monitoring the energy of the pulses as the pulses are being delivered to the patient. Such an apparatus may include an excimer, pulsed laser, and a beam homogenizer and a spatial modulator in the optical path of the laser. First electronic circuitry controls the laser and spatial modulator in accordance with entered data indicative of the predetermined treatment sequence of pulses for the patient. Second electronic circuitry produces reference values indicative of the energy of laser pulses which should be produced by the laser, the reference value being calculated in accordance with separately entered data indicative of the predetermined treatment sequence of pulses for the patient. Advantageously, the first and second electronic circuitry are separate, programmable digital computing devices.

A photo detector produces a monitoring signal related in value to the energy of laser pulses delivered to the patient. Further electronic circuitry compares the monitoring signal with the corresponding reference value calculated by the second electronic means.

The foregoing is intended as a convenient summary of this disclosure. However, the scope of the invention intended to be covered is indicated by the patent claims.

BRIEF DESCRIPTION OF THE DRAWINGS

FIG. 1 is a plan view of a two surgical station laser eye surgery system;

FIGS. 2(a) and (b) are, respectively, vertical and horizontal cross-sectional views of the optical path employed in the system of FIG. 1 for delivering laser pulses to the cornea of the patient;

DETAILED DESCRIPTION OF PREFERRED EMBODIMENTS

Figure 3:
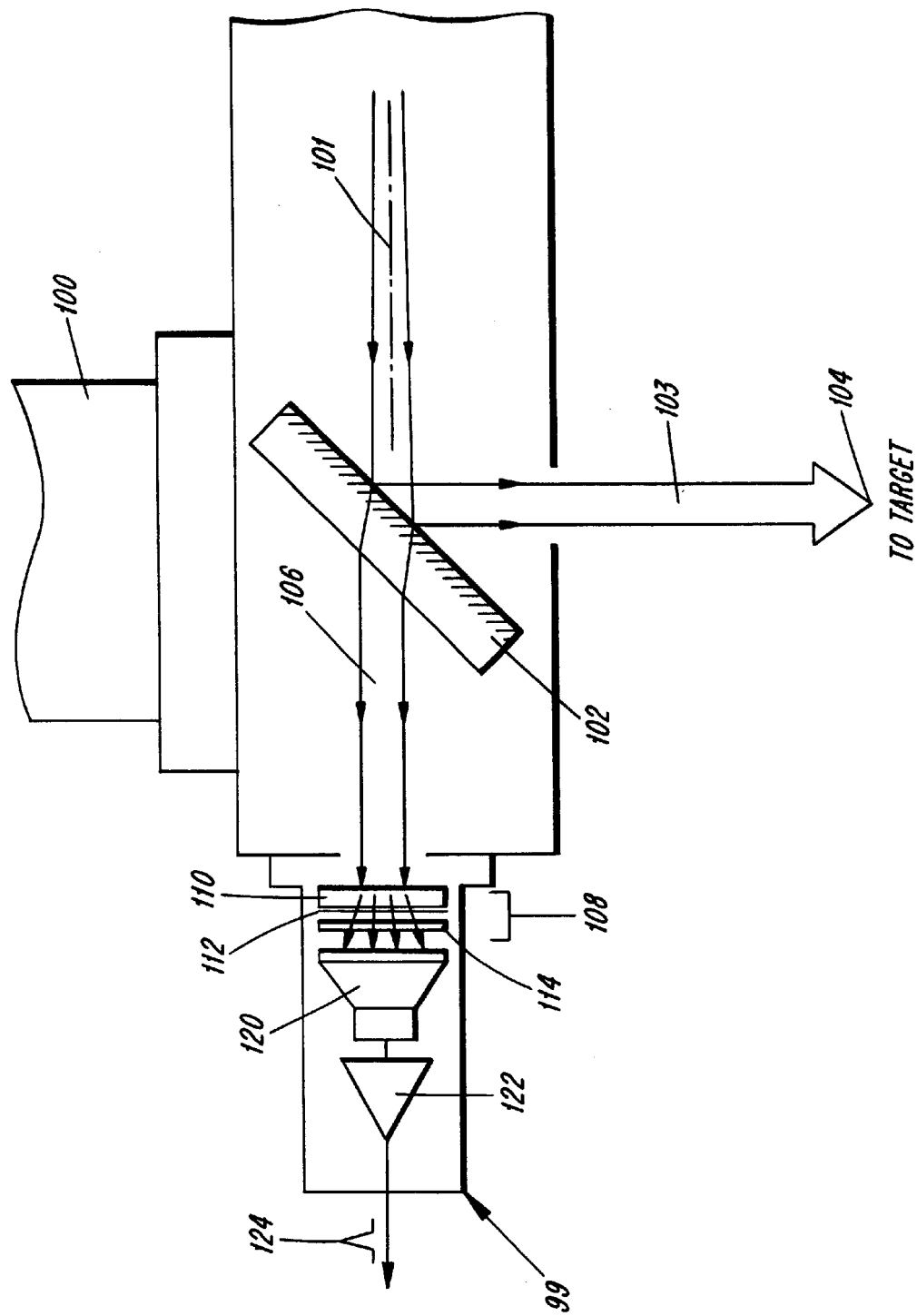
FIG. 3 is a horizontal cross-sectional view of a laser energy monitor in accordance with a preferred embodiment of the present invention.

The fail-safe systems disclosed are based on the control and monitoring of the energy in the laser beam exiting the optical rail and beam controlling optics of a laser surgery system. In preferred embodiments, the fail-safe system includes a laser energy monitor, analog-to-digital converter, and a programmed monitoring computer.

The monitoring system may be used, for example, in the two patient ophthalmic surgical arrangement shown in FIG. 1. In such a case, two identical laser energy monitors may be installed at the ends of the right and the left laser beam delivery systems (surgical stations) after the end 45° turning mirror. As discussed in greater detail below, each energy monitor may consist of a glass fluorescence filter, converting laser radiation into fluorescence light, and a silicon photo diode for light detection. To operate the diode and the signal amplifier in linear modes, several neutral density filters are used. The amplified photo diode signal goes to the analog-to-digital converter (preferably a circuit card installed into the monitoring computer or an additional computer).

Two independent computers may be used in the most preferred embodiment of the present invention. One computer is the treatment computer, the second computer is the monitoring or fail-safe computer. The treatment computer drives the iris/slit/axis motors in the spatial modulator and generates the appropriate trigger pulses to the laser according to a treatment/calibration algorithm.

The monitoring computer measures, records, and monitors the energy detected by the energy detector for each pulse fired. The monitoring computer compares the energy values of the treatment algorithm to a predetermined calibration curve and simultaneously runs fail-safe algorithms. The treatment algorithm and the monitoring algorithm are equivalent. The monitoring computer receives the triggering signal sent to the laser by the treatment laser. Live and simultaneous monitoring of the entire treatment dose is performed by the system.

To avoid rather complicated calculations of iris, mask or spot geometrical area and the influence of functional non-linearity of the photo diodes and A/D converter or measurement accuracy, a calibration curve approach may be used. A calibration curve is generated at the beginning of every surgery period. This is accomplished with an initial calibration process. The calibration curve may be generated by running a calibration algorithm on the treatment laser and measuring and storing measured pulse energy values for each slit and iris setting from 6.0 mm down to 1.0 mm with 0.5 mm increments. The fail-safe computer program generates a calibration curve based on the photo diode signal value of an average of 20 consecutive laser pulses taken at each position of the iris and slit. When a treatment ablation algorithm is executed, the monitoring computer receives, after every laser pulse the digitized photo detector signal which is compared to a reference value obtained from the calibration curve, the reference value indicating the expected energy value for the particular spatial dimensions of the pulse then being administered.

The monitoring computer software compares the measured energy value with a reference value determined from the treatment parameters and treatment algorithm. Even though the system monitors laser pulse energy, its comparison with reference values from the calibration curve for the proper iris/slit dimension is equivalent to monitoring the energy of the ablating laser beam.

The monitoring computer may be programmed with values of acceptable deviation between the monitored energy and reference energy values. For example, an acceptable deviation in treatment energy may include +/−10% deviation range from the calibration curve. If 10 consecutive laser pulses are outside of the above assigned ranges, the monitoring computer initiates a continuous warning beep, and after 3 seconds will interrupt the laser triggering through a relay block unless the laser operator does so earlier.

Both the treatment and monitoring computers track and store all data of a patient's treatment algorithm, energy etc. and if the treatment is interrupted or stopped, the treatment data will be available to resume treatment after the problem is resolved. Fail-safe features incorporated into the system include a maximal/minimal range of treatment energy, storage of treatment data, and an uninterruptable power supply system to maintain both the treatment computer and the monitoring computer in the event of a power failure.

Monitoring proper operation of the iris/slit mechanism is a function of the monitoring computer software, and is accomplished through comparisons of measured energy values by the photo diode with expected energy values for the specific treatment algorithm and the particular iris/slit dimensions called for by the algorithm. For example, the treatment computer could signal the iris to be 4 mm. However, the iris may be "stuck" at 5 mm. The fail-safe system would monitor the pulse and indicate too high an energy value as compared with the reference value for the expected 4 mm iris. A value associated with the "stuck" 5 mm iris would be recorded.

Another feature of the laser dual computer fail-safe system requires the operator to enter the patient treatment data twice, once into the treatment computer and a second time into the monitoring or fail-safe computer. This dual entry requirement provides for an opportunity to double-check the current patient name, eye, and desired correction for refractive error.

Details of the system of the present invention will now be described with reference to the drawings.

FIG. 3 is a cross-sectional side elevation of a portion of an arm of the system of FIG. 1 including a laser energy monitor 99 and a surgical microscope mount 100. A laser beam from the optical rail and shuttling device is shown at 101. The pulses making up the beam have already been spatially modulated. The beam impinges on a beam-splitter 102. In preferred embodiments, the beam splitter is a fused silica coated glass plate with a principle plane oriented at a 45° angle with respect to the laser beam 101. The front surface of the plate 102 may reflect approximately 95% of the energy of the laser beam (reflected beam 103) to the target as indicated at 104. A low energy transmitted beam 106 passes through the beam-splitter and impinges on a detector optical system 108. In preferred embodiments the detector optical system includes a glass filter/diffuser 110 which diffuses the laser light.

Advantageously, a fluorescent media 112 is located at the diffuser. The fluorescent media may have the effect of changing the wavelength of the incident light. For example, diffused 193 nm laser radiation may be converted into blue-green fluorescent light.

One or more neutral density filters 114 may be provided to reduce the intensity of the light received by the photo detector, such as photo diode 120. This intensity reduction is provided to permit the photo detector and associated analog amplifier 122 to operate in a generally linear response mode across a range of expected incident light energies.

The amplifier 122 produces a signal 124. In preferred embodiments, the signal is a voltage pulse which is selected by time-windowing circuitry in the monitoring computer. The windowing is triggered by the triggering of the laser system to produce a treatment pulse. The peak height of the voltage pulse is used as an indication of the energy of the treatment pulse delivered to the patient, as will be discussed below.

Figure 4:
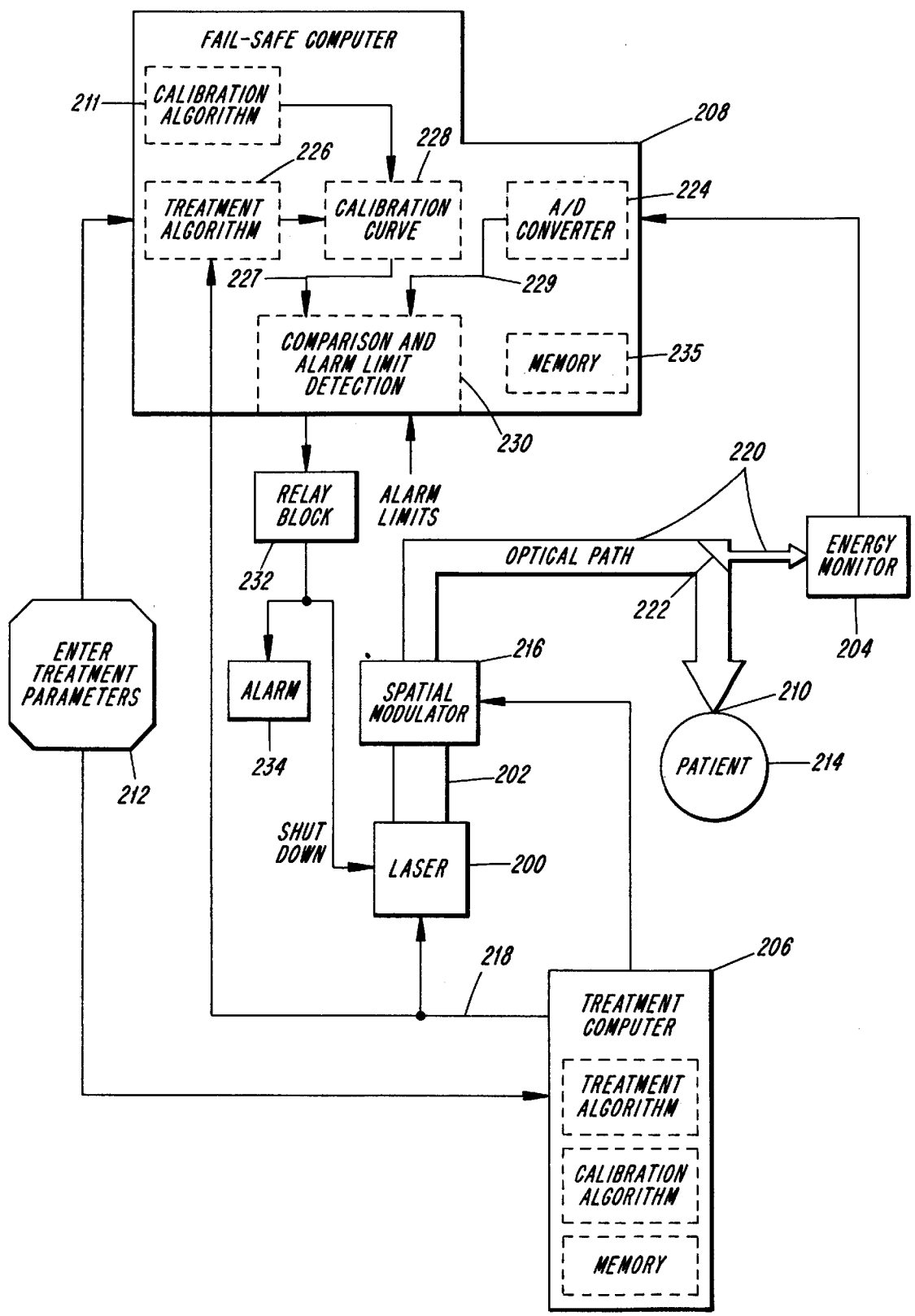
FIG. 4 is a schematic block diagram illustrating process and apparatus aspects of the disclosed system for producing and monitoring laser pulses delivered to the cornea of a patient in accordance with the present invention.

FIG. 4 is a schematic block diagram illustrating aspects of the method and system of the present invention. The system includes a laser 200, optical rail 202, energy monitor 204, treatment computer 206 and fail-safe computer 208.

In operation, the system is initially calibrated by placing a laser light energy detector at the location 210 and producing a series of test pulses having various spatial modulation under the control of the calibration algorithm of the treatment computer. At the same time energy is monitored using the energy monitor 204 and fail-safe computer 208. The fail-safe computer develops a calibration curve or data using the calibration algorithm 211 and monitored energy values.

More specifically, in the calibration mode, an average of measured energy values from the A/D converter are associated with the various spatial modulator settings. The result is a calibration curve or look-up table which correlates various spatial modulator settings with an average voltage measurement from the energy monitor during the calibration mode.

Treatment parameters are entered for a particular patient as indicated at 212. The treatment parameter may include sphere correction, cyl correction and cyl axis values. The data entry is made separately to both the treatment computer 206 and the fail-safe computer 208. The patient 214 is readied for surgery.

The treatment computer 206 generates a treatment sequence of pulses and controls the spatial modulator 216 in accordance with commands derived by a conventional treatment algorithm from the treatment parameters. The laser 200 is triggered by signals on control line 218. These trigger signals are simultaneously provided to the fail-safe computer 208.

Pulses produced by the laser 200 are spatially modulated and travel along optical path 220. The beam splitter 222 reflects the pulses to the patient's cornea and transmits a portion of the beam to the energy monitor 204. Signals from the energy monitor are applied to the A/D converter 224, which may be part of the circuitry hardware of the fail-safe computer 208.

Pulses from control line 218 and data entered as treatment parameters are processed by the treatment algorithm 226 resident in the fail-safe computer 208. The monitoring computer calls up a valve from the calibration curve or look-up table which corresponds to the spatial modulation of the pulse being administered. The result is a reference value related to the prescribed energy for the being pulse delivered to the patient. This reference value is indicated at 227. The reference value is compared to a monitor energy value 229 derived from the signal from the energy monitor 204. The comparison is indicated at 230.

Alarm limits may be input to the fail-safe computer 208. The alarm limits are employed to generate a control or alarm signal which is output to the relay block 232. The relay block may trigger alarm 234 or command a shut down of the laser 200.

Calibration data, treatment parameters, energy monitor data, alarm limits and comparison data may be stored in a memory 235 in fail-safe computer 208.

The system described above has been tested in an ophthalmic surgery excimer laser system. The laser output at each surgical station was set at 38 mJ at 6 mm of iris opening by adjusting the high voltage setting of the excimer laser. The corresponding digital value of photo diode signal was set as a reference energy value. Initial qualitative tests at 6 mm iris/slit opening included blocking of about 12% of laser aperture at different points. In all cases, the fail-safe mechanism worked properly reacting to the energy deficiency in the beam. Quantitative tests consisted of intentional decrease/increase of laser energy output by adjusting the excimer laser voltage at different iris/slit positions. A JMAX 43/EM400 energy meter was used to measure the output laser energy at the treatment plane. The following table presents the test results:

| Iris/slit opening (mm) | | Initial energy, | Shut Down Energy | | | |
|---|---|---|---|---|---|---|
| Iris | Slit | mJ | mJ | + % | MJ | - % |
| 1.5 | open | 2.6 | 2.9 | 11 | 2.3 | 11 |
| 6.0 | 2.0 | 14 | 15.5 | 11 | 12.5 | 11 |
| 3.0 | open | 10.0 | 11.0 | 10 | 9.0 | 10 |
| 6.0 | 4.5 | 25 | 27.5 | 10 | 22.5 | 10 |
| 5.0 | open | 27 | 30.0 | 11 | 24.4 | 10 |

Additional tests were conducted to simulate a variety of malfunctions of the iris/slit mechanism. This was accomplished by entering values in the treatment algorithms that simulated both partial and complete "sticking" of both the iris and slit while operating the monitoring fail-safe computer with the correct algorithms.

In all cases, the fail-safe system detected the errors by sounding an alarm and recording energy values that were either too high or too low with respect to the expected value for the proper iris or slit dimensions.

The test results show that the fail-safe mechanism operated in accordance with its design. The dual computer fail-safe method monitors the operation of the iris/slit mechanism, the quality of the optics, firing mechanism and ablation algorithm as well as the laser itself during the actual patient treatment. The results show that the fail-safe mechanism operated in accordance with its design. Its implementation is expected to provide higher safety level for patient laser refractive treatments.

While the present invention has been described with reference to certain preferred embodiments, the scope of the invention to be protected is determined by the following claims and their appropriate range of equivalents.

I claim:

1. A method for monitoring a laser surgery system which produces a sequence of laser pulses of varying spatial dimensions in accordance with a treatment algorithm run by a treatment computer, comprising the steps of:

beam splitting each laser pulse in a sequence of calibration pulses of various spatial dimensions, so as to apply a predetermined portion of light energy of each pulse to a photo detector;

providing output signals of the photo detector to a monitoring computer and associating the output signals of the photo detector with corresponding pulses of various spatial dimensions to obtain a reference value for each type of pulse;

beam splitting a sequence of treatment laser pulses of various spatial dimensions so as to apply the predetermined portion of the light energy of each treatment pulse to the photo detector and to simultaneously apply another portion of the energy of each pulse to treat a patient; and comparing an output signal from the photo detector corresponding to a treatment laser pulse with a reference value for that type of pulse, wherein the reference value is obtained by using a treatment algorithm in the monitoring computer to identify the type of pulse which should be being administered in the treatment sequence and to select the corresponding reference value.

2. The method of claim 1, wherein the treatment algorithm run in the treatment computer is the same treatment algorithm used by the monitoring computer.

3. The method of claim 2, wherein treatment parameters are separately applied to the treatment computer and monitoring computer.

4. The method of claim 3, wherein the surgery is laser keratotomy and the treatment parameters are refractive and astigmatism corrections appropriate for the patient.

5. The method of claim 4, wherein the treatment parameters are used by the treatment computer to select iris settings and slit dimensions which vary the spatial dimensions of the laser pulses.

6. A system for monitoring laser pulses produced by a laser system in accordance with a predetermined treatment sequence and directed at the cornea of a patient to modify the cornea by photo ablation and for continuously verifying that the predetermined treatment sequence of pulses is being delivered to the patient comprising an electro-optic detector, a beam splitter for simultaneously directing one portion of the electromagnetic energy of the laser pulses along an optical path to the electro-optic detector and another portion of the energy of the pulse to the cornea of the patient, a diffuser in the optical path for receiving the laser pulse from the beam splitter, a fluorescent media in the optical path for converting the diffused, laser pulses to fluorescent light detected by the electro-optic detector; and a monitoring computer for comparing an output signal of the electro-optic detector with a reference value for the monitored pulse, said reference value being calculated in accordance with separately entered data indicative of the predetermined treatment sequence of different energy pulses and from signal values for such pulses measured by the electro-optic detector during a preliminary calibration.

7. The system of claim 6, wherein the beam splitter directs approximately 5% of the energy of the laser pulse to the diffuser, the balance of the energy being directed to the cornea of the patient.

8. The system of claim 6, further comprising neutral density filters in the optical path for reducing the intensity of the electromagnetic radiation received by the electro optic permit the electro optic to operate in a linear mode.

9. The system of claim 6, wherein the beam splitter is the last optical element in the optical path leading to the cornea of the patient and wherein the light detected by the electro-optic detector is a known fraction of the total energy delivered to the beam splitter.

10. The system of claim 6, wherein the beam splitter has a front surface mirror which reflects laser pulses to the cornea of the patient.

11. The system of claim 6, wherein the beam splitter acts as a turning mirror and reflects laser pulses from its front surface directly to the cornea of the patient.

12. The system of claim 11, wherein laser light received by the electro-optic detector is transmitted through the beam splitter.

13. A system for monitoring laser pulses directed at the cornea of a patient during which treatment pulses are produced by a laser system controlled by a treatment computing device in accordance with entered data for a treatment sequence for the patient and for verifying that the patient's treatment sequence of pulses is being delivered to the patient during the treatment sequence comprising:

an electro-optic detector;

a beam splitter for splitting laser pulses and directing a first fraction of the energy of calibration laser pulses to the electro-optic detector during calibration to produce calibration signals and, during the treatment sequence, for directing the first fraction of energy of at least some treatment pulses to the electro-optic detector to produce treatment monitoring signals and for directing a second fraction of the energy of such pulses to the cornea of the patient; and a failsafe computing device, for producing reference values indicative of the expected treatment monitoring signals for treatment pulses produced during the treatment sequence, said reference values being determined from data entered into the failsafe computing device separately from the data entered into the treatment computing device, said separately entered data being indicative of the patient's treatment sequence, and from the calibration signals for such pulses measured during calibration; and for comparing the treatment monitoring signals for at least some of the treatment pulses with corresponding reference values produced by the failsafe computing device to provide an indication of the performance of the system while the treatment sequence is ongoing.

14. The system of claim 13, wherein an alarm signal is produced as an indication of the performance of the system when comparison of the monitoring signals with the reference values indicates that the monitoring signals for a predetermined number of treatment pulses have deviated a predetermined amount from the corresponding reference values.

15. The system of claim 13, wherein each comparison is initiated responsive to a signal triggering the laser to generate a treatment pulse.

16. The system of claim 13, wherein the separate data entry and comparison are performed on a general purpose digital computer.

17. The system of claim 16, wherein the treatment computing device and the failsafe computing device are implemented in the same general purpose digital computer.

18. The system of claim 13, wherein different types of treatment pulses are characterized by different energies and wherein reference values are provided for each type of pulse employed in the treatment sequence.

19. The system of claim 13 wherein the beam splitter is the last optical element in an optical path leading to the cornea of the patient.

20. The system of claim 13, wherein the second fraction of energy of the laser pulses is reflected from a front surface mirror of the beam splitter directly to the cornea of the patient.

21. The system of claim 20, wherein the first fraction of energy of the laser pulses is transmitted through the beam splitter on an optical path leading to the electro optic detector.

22. A system for monitoring laser pulses directed along an optical path leading to the cornea of a patient comprising:

an electro-optic detector;

a beam splitter that is the last optical element in the optical path leading to the cornea of the patient, wherein the beam splitter directs a first predetermined fraction of the energy of at least some laser pulses to the electro-optic detector during calibration to produce calibration signals, and, during a treatment sequence, the beam splitter directs the first predetermined fraction of energy of at least some treatment pulses to the electro-optic detector to produce treatment monitoring signals and directs a second fraction of the energy of such pulses to the cornea of the patient; and a failsafe computing device for monitoring the performance of the system while the treatment sequence is ongoing by comparing the treatment monitoring signals for at least some of the treatment pulses with corresponding reference values derived from the calibration signals.

23. The system of claim 22 wherein the beam splitter has a front surface mirror which reflects the laser beam to the cornea of the patient.

24. The system of claim 22, wherein the beam splitter acts as a turning mirror and reflects laser pulses from its front surface directly to the cornea of the patient.

25. The system of claim 24, wherein laser light received by the electro-optic detector is transmitted through the beam splitter.

* * * * *